(12) United States Patent
Garipoglu et al.

(10) Patent No.: US 12,721,541 B2
(45) Date of Patent: Sep. 1, 2026

(54) PORTABLE BREATH ANALYSIS DEVICE SYSTEM AND A METHOD THEREOF

(71) Applicant: BAHCESEHIR UNIVERSITESI, Istanbul (TR)

(72) Inventors: Gokcen Berat Garipoglu, Istanbul (TR); Mustafa Yunus Konmaz, Istanbul (TR)

(73) Assignee: BAHCESEHIR UNIVERSITESI, Istanbul (TR)

( * ) Notice: Subject to any disclaimer, the term of this patent is extended or adjusted under 35 U.S.C. 154(b) by 387 days.

(21) Appl. No.: 18/290,223

(22) PCT Filed: Apr. 28, 2022

(86) PCT No.: PCT/TR2022/050392

§ 371 (c)(1),
(2) Date: Nov. 10, 2023

(87) PCT Pub. No.: WO2022/240376

PCT Pub. Date: Nov. 17, 2022

(65) Prior Publication Data

US 2024/0237913 A1 Jul. 18, 2024

(30) Foreign Application Priority Data

May 11, 2021 (TR) ................................ 2021/008046

(51) Int. Cl.

| | |
|---|---|
| ***A61B 5/00*** | (2006.01) |
| ***A61B 5/08*** | (2006.01) |
| ***A61B 5/097*** | (2006.01) |

(52) U.S. Cl.

CPC ............ *A61B 5/082* (2013.01); *A61B 5/0004* (2013.01); *A61B 5/097* (2013.01); *A61B 5/486* (2013.01);

(Continued)

(58) Field of Classification Search

CPC ....... A61B 5/082; A61B 5/0004; A61B 5/097; A61B 5/486; A61B 5/6898;

(Continued)

(56) References Cited

U.S. PATENT DOCUMENTS

| | | | | |
|---|---|---|---|---|
| 4,931,404 A * | 6/1990 | Kundu | .................. | G01N 33/64 422/86 |
| 5,071,769 A * | 12/1991 | Kundu | .................. | A61B 5/083 436/178 |

(Continued)

FOREIGN PATENT DOCUMENTS

| | | |
|---|---|---|
| EP | 2461747 | 6/2012 |
| TR | 2019/16753 | 10/2019 |
| TR | 2019/15900 | 12/2020 |

*Primary Examiner* — May A Abouelela
(74) *Attorney, Agent, or Firm* — Crose Law LLC; Bradley D. Crose

(57) ABSTRACT

The present invention relates to a portable breath analysis device system and a method thereof that helps healthy nutrition and weight loss by allowing for detecting the intolerant foods by means of analyzing the respiratory gases received from the person's breath. The present invention particularly relates to a portable breath analysis device system and a method thereof that simultaneously and instantaneously measures acetone, ammonia, nitric oxide, ethanol, carbon monoxide, and hydrogen gases in the breath of a person, that allows for monitoring and regulating a person's carbohydrate (sugar), fat, and protein consumption with a computer-based method by transferring the data obtained from these measured gases to a mobile device.

20 Claims, 2 Drawing Sheets

(52) U.S. Cl.
CPC .... *A61B 5/6898* (2013.01); *A61B 2560/0431* (2013.01)

(58) Field of Classification Search
CPC .......... A61B 2560/0431; A61B 5/0002; A61B 5/083; G01N 33/497
See application file for complete search history.

(56) References Cited

U.S. PATENT DOCUMENTS 5,174,959 A * 12/1992 Kundu .................. G01N 33/64 436/128
9,299,238 B1 * 3/2016 Ahmad .................. H04W 4/80
9,643,186 B1 * 5/2017 Ahmad ................ G01N 33/542
10,226,201 B2 3/2019 Ahmad et al.
10,285,642 B2 * 5/2019 Ahmad .................. A61B 5/082
10,682,072 B2 6/2020 Ratto et al.
11,510,592 B2 * 11/2022 Gabbai .................. A61B 5/097
11,721,533 B1 * 8/2023 Verbeck, IV ........... H01J 49/26 73/23.23
11,841,372 B1 * 12/2023 Verbeck, IV ........ G01N 33/948
12,150,752 B2 * 11/2024 Rigas .................. A61B 5/1477
2003/0208133 A1 * 11/2003 Mault .................. G01N 33/497 600/531
2004/0236244 A1 * 11/2004 Allen ........................ C12P 7/28 600/532
2015/0250408 A1 * 9/2015 Ssenyange ......... G01N 33/0016 600/532
2015/0272475 A1 * 10/2015 Buess .................... A61B 5/742 600/531
2019/0261891 A1 8/2019 Ahmad et al.
2019/0374131 A1 * 12/2019 Ross .................... H04N 9/8205
2020/0029858 A1 * 1/2020 Reddy .................... G16H 40/67
2020/0170545 A1 6/2020 Reddy
2020/0337594 A1 10/2020 Reddy
2021/0085247 A1 * 3/2021 Meirav ................ A61B 5/0833
2021/0169370 A1 * 6/2021 Vicario .................. A61B 5/097
2022/0020488 A1 * 1/2022 Kennedy ................ G16H 20/40
2022/0039690 A1 * 2/2022 Rigas ..................... A61B 5/082
2022/0095949 A1 * 3/2022 Allende ................. A61B 5/082
2022/0120751 A1 * 4/2022 Hanna ............. G01N 33/57484
2022/0265945 A1 * 8/2022 Schranz .................... G01J 3/36
2022/0287587 A1 * 9/2022 Rigas ..................... A61B 5/082
2022/0313110 A1 * 10/2022 Hu .......................... G06F 3/167
2022/0317122 A1 * 10/2022 Lapidot ............ G01N 33/56983
2022/0341911 A1 * 10/2022 Allsworth .............. A61B 5/082
2022/0354383 A1 * 11/2022 Jia .......................... A61B 5/087
2022/0364984 A1 * 11/2022 Kääriäinen ............. G01J 3/433
2023/0012349 A1 * 1/2023 Gamache ............... G16H 10/40
2023/0068371 A1 * 3/2023 Hanna .................. G01N 33/497
2023/0175042 A1 * 6/2023 Aguren ................ G01N 1/4022 435/6.11
2023/0190149 A1 * 6/2023 Kiyama ............... G01N 33/497 600/361
2024/0110919 A1 * 4/2024 Chau ..................... G01N 21/80

* cited by examiner

PORTABLE BREATH ANALYSIS DEVICE SYSTEM AND A METHOD THEREOF

TECHNICAL FIELD OF THE INVENTION

The present invention relates to a portable breath analysis device system and a method thereof that helps healthy nutrition and weight loss by allowing for detecting the intolerant foods by means of analyzing the respiratory gases received from the person's breath.

The present invention particularly relates to the portable breath analysis device system and a method thereof that simultaneously and instantaneously measures acetone, ammonia, nitric oxide, ethanol, carbon monoxide, and hydrogen gases in the breath of a person, that allows for monitoring and regulating a person's carbohydrate (sugar), fat, and protein consumption with a computer-based method by transferring the data obtained from these measured gases to a mobile device.

STATE OF THE ART

In the studies carried out to date, it has been determined by different analytical techniques that there are more than 1000 volatile organic compounds (VOC) in human breath and concentrations thereof vary from ppm (parts per million) to ppt (parts per trillion). The important determinants of the compounds in the breath are the nutrients and diet, as well as the time the individual nutrients in the digestive tract remain, intestinal flora, metabolism, systemic inflammatory conditions, and redox capacity. A high-fat diet has been shown to increase the level of Nitric Oxide (NO) in the breath. Nitric Oxide, on the other hand, has an anti-inflammatory effect by being produced at a certain level in the body in case of inflammation, while higher levels than expected may give an idea regarding the degree of inflammation. There are studies showing that long-term high-fat diets increase inflammation.

One of the most important VOCs in breath is the ammonia (NH3) molecule. The ammonia molecule is the product of the nitrogen cycle resulting from protein metabolism. As a result of high protein diets, an increase in the levels of acetone and ethanol, especially NH3, is observed in the breath. The NH3 molecule in the blood of a healthy person is removed by the liver and kidneys. High protein intake or any malfunction that may occur in these organs causes an increase in NH3 levels in the blood, which causes the diffusion of NH3 molecule to the lungs and an increase in the amount in the breath. In this case, following the effects of the protein content of the diets on the person and making the necessary adjustments in the diet will provide healthier weight control.

14% of the Hydrogen (H2) gas produced by the bacterial flora in the digestive tract is removed by breathing. Due to the increase in the amount of H2 in the breath in digestion/absorption disorders of simple carbohydrates (CHO), the H2 breath test is used for the diagnosis of malabsorption. Complex CHOs remain in the digestive tract for a long time and cause the production of methane (CH4) together with H2. This prevents the continuation of diets in weight control. Practical measurement in the breath will make it possible to separate the foods that cause digestive problems.

In the state of the art, in the abstract section of the description of the patent document numbered "TR2019/16753" it is stated that "the invention relates to devices for measuring glucose. In particular, the invention relates to a device that measures glucose by breathing. The characteristics of our invention is a device that is small enough to fit in the palm of the hand for diabetics, that measures the breath blown into the device with the acetone sensor therein, and that measures blood glucose from the circuit."

In the state of the art, abstract section of the patent document numbered "TR2019/15900" have information such as "the invention relates to a device that measures blood glucose with the help of measuring the amount of ketones by breathing using at least one gas sensor and that warns people such as parents and doctors regarding the user. The routine finger piercing of diabetics is prevented by means of said device".

In the state of the art, patent application numbered "US20190261891A1" mentions a portable device for analyzing a user's breath sample in the clinic or in the home of the patient. A breath analysis device into which a user exhales a breath sample is capable of venting an initial portion of the breath sample from the device, and routing a second portion of the breath sample into a disposable cartridge containing an interactant. The device may include a sensor, such as a pressure sensor, for detecting the initiation of exhalation, and may include a controller that switches a valve during the exhalation process to route a desired portion of the breath sample into the cartridge. After the exhalation process, an LED/photodiode arrangement, or another type of optical sensor, may be used to measure a color change produced by a chemical reaction in the cartridge, to thereby measure a concentration of a ketone or other analyte in the breath sample.

In the state of the art, the patent application numbered "US20200170545A1" mentions Real-time breath ketone gas detectors and systems that can be integrated into mobile devices, and a method thereof. It comprises an opening, providing a flow path through which a person breathes, a sensor, providing a ketone signal corresponding to a concentration of a respiratory component in exhalations of the person and including metabolic data, Wherein the concentration of the respiratory component is associated with a level of ketone bodies in blood of the person, a display, and an electronic circuit, receiving the ketone signal and the metabolic data and providing a visual indication of the ketone signal and the metabolic data on the display.

In the state of the art, the patent application numbered "EP2461747A1" mentions a method that effectively monitors and/or detects the concentrations of the contents of chemicals (e.g. biomarkers) in exhaled breath. The method of the invention is used to detect a measurable characteristic of the gas sample (where the measurable characteristic includes the mass, amount, concentration, flow rate or a volume of the gas sample of the target chemical in the gas sample); to determine an effect caused by exposure to radiation; to measure a biological response to a radiation exposure.

In the state of the art, it is reported that the measurement of acetone in the breath, which is one of the ketone bodies formed by the ketogenic diet, which is a high-fat, low-CHO diet, is also a reliable indicator for ketosis.

In the state of the art, there are studies showing that long-term high-fat diets increase inflammation by using nitric oxide that can give an idea regarding the degree of inflammation if it is higher than expected levels.

In the state of the art, some of the data to be taken for analysis from breath are performed by high cost laboratory measurements. Its implementation is costly and impractical. Repeated and instant measurements cannot be performed. In addition, only one or two of the gases in the breath are measured in these measurements, and multiple gas analysis cannot be performed at the same time.

In the state of the art, the reference method used for breath gas analysis in clinical chemistry laboratories is GC-MS (Gas chromatography mass spectrometry). However, this device is not a practical method since it is not portable and requires a fixed platform, is quite expensive in terms of price, complex procedures are involved in both the collection and preliminary preparation of the samples, and it requires technicians who has the knowledge, however, it allows it to be used as a reference method.

Consequently, the disadvantages disclosed above and the inadequacy of available solutions in this regard necessitated making an improvement in the relevant technical field.

OBJECTS OF THE INVENTION

The most important object of the present invention is to provide information about nutrition and metabolism status and to give nutritional advice for a specific situation by using the computer-based method included therein, based on the gases measured by the device, which is the subject of the invention, while determining the situation with the device that analyzes more than one gas.

Another important object of the present invention is to provide a non-invasive, sensitive method with immediate results instead of invasive methods that are laborious and painful for the patient. Thus, the breath analysis device is considered a safer method in terms of disease diagnosis and monitoring of metabolic status since the amount of VOCs in the breath can be affected by metabolic disorders or diseases.

Yet another object of the present invention is to not contain any risk for the person to whom it is applied, to be easily repeatable, and to not require qualified personnel for evaluation.

Another object of the invention is to perform real-time monitoring and to be easily portable of the breath analysis device. Therefore, the practical application of the portable breath analysis method will provide great convenience and comfort for future studies, and the data that can be obtained will shed light on new studies.

Yet another important object of the present invention is to analyze the user's breath, to evaluate the metabolic data of the person, especially in the treatment of obesity, and to use it to follow the effectiveness of the diets applied. Thus, more than one gas can be measured at the same time and it will also contribute to the reduction of health expenditures.

Yet another object of the present invention is to provide individual nutrition control with instant and repetitive measurements of the device to be used specifically for the person, and also to follow the data instantly by the expert and to make correct directions.

Yet another object of the present invention is to contribute to social health and healthy aging by means of regulating healthy nutrition and metabolic health, preventing chronic diseases, especially diabetes, or supporting treatment processes.

Yet another object of the present invention is to measure the acetone in the breath and enable it to be used to monitor the effectiveness of ketogenic weight loss diets.

REFERENCE NUMERALS

Figure 1:
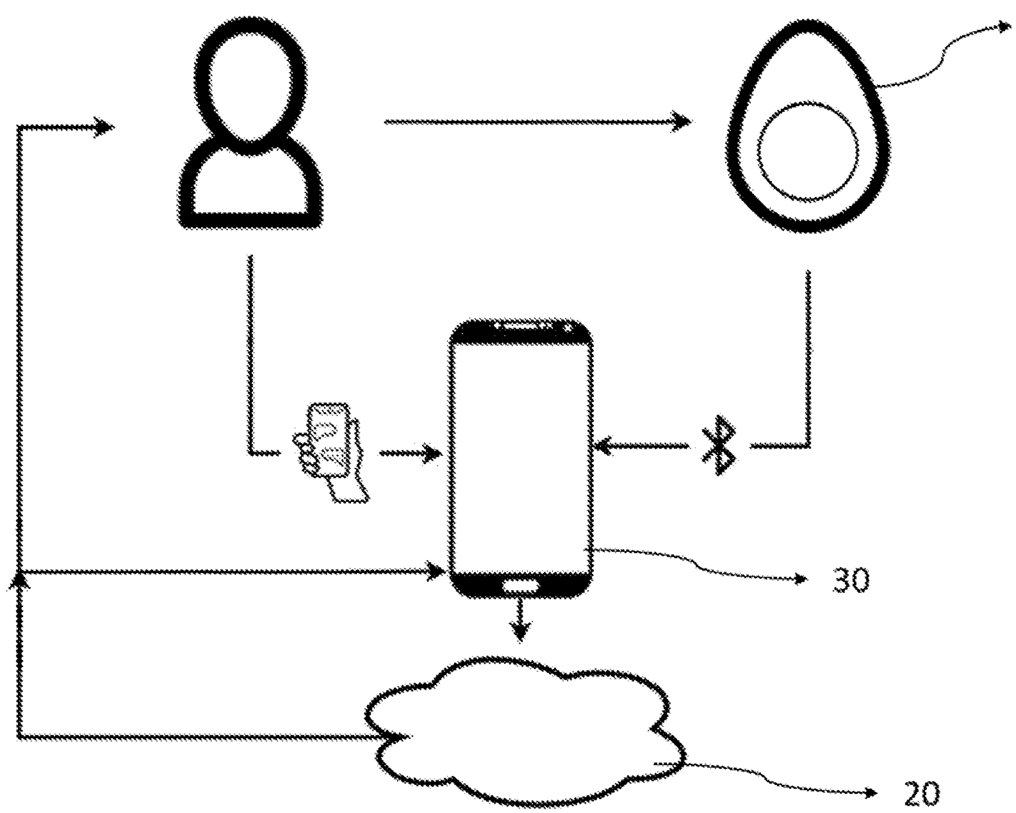
FIG. 1 is the drawing that illustrates the diagram view of the elements of the analysis system according to the present invention.
Figure 2:
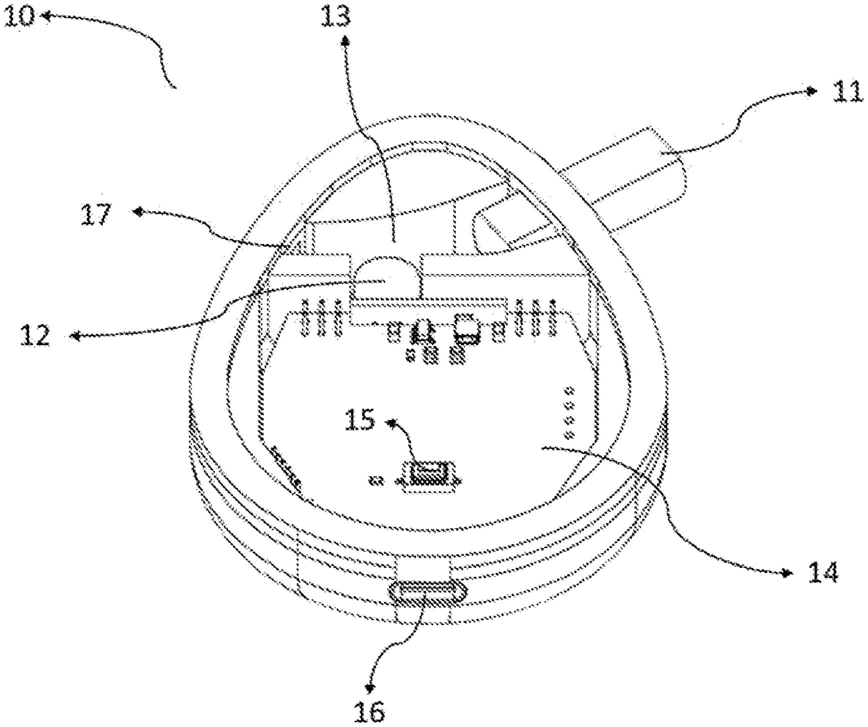
FIG. 2 is the drawing that illustrates the perspective view of the portable device of the analysis system according to the present invention.
Figure 3:
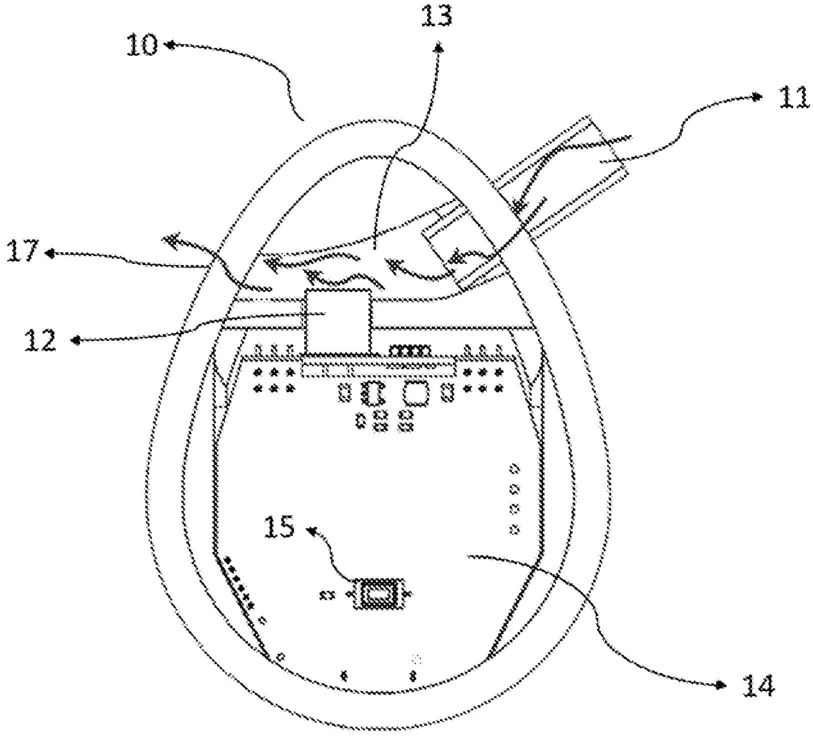
FIG. 3 is the drawing that illustrates the front open view of the portable device of the analysis system according to the present invention.
Figure 4:
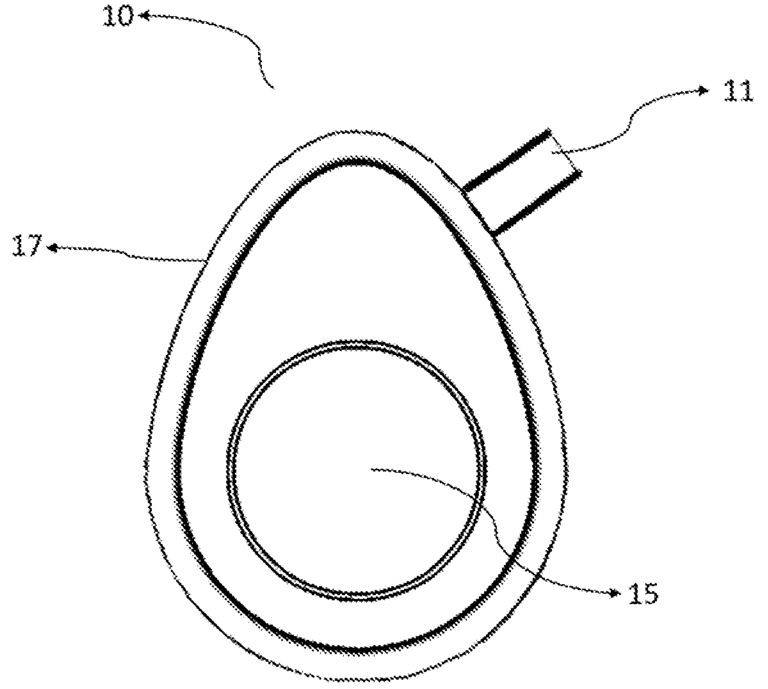
FIG. 4 is the drawing that illustrates the front closed view of the portable device of the analysis system according to the present invention.

10. Breath Measuring Device
11. Blowing Mouthpiece
12. Gas Sensor
13. Breath Chamber
14. Electronic Circuit Card
15. Button
16. Charge Input Port
17. Air Outlet Opening
20. Server
30. Mobile Device

DESCRIPTION OF THE INVENTION

The system according to the present invention comprises a breath measuring device (10) that simultaneously and instantaneously measures acetone, ammonia, nitric oxide, ethanol, carbon monoxide, and hydrogen gases in the breath of the person, a server (20) that enables monitoring and regulating a person's carbohydrate (sugar), fat and protein consumption with a computer-based method by transferring the data obtained from these measured gases to a mobile device (30), and the mobile device (30) that enables said data to be displayed.

The breath measuring device (10) simultaneously and instantaneously measures Carbon Monoxide (CO), Nitrogen Dioxide (NO2), Ethanol (C2H5OH), Hydrogen (H2), Ammonia (NH3), Methane (CH4), Acetone (C3H6O) gases in the breath of the person.

These gases are measured separately with different gas sensors (12). The breath measuring device (10) provides a portable, practical measurement that combines three different gas sensors (12) in a single device. The user will be able to follow these measurements individually or share them with their physician/dietitian. In addition, the data obtained from these measured gases are transferred to the mobile device (30) by the cloud server (20), allowing the person to monitor and regulate the carbohydrate (sugar), fat, and protein consumption. In addition, it also helps to identify foods that cause intolerance, helping healthy eating and weight loss.

The breath measuring device (10) has a blowing mouthpiece (11) that allows the user to blow his/her breath, a gas sensor (12) for measuring the gases in the breath, a breath chamber (13), in which the blown breath is transmitted to the gas sensor (12), an electronic circuit card (14) that enables the wireless transmission of the received data to the mobile device (30) and gives the user warnings of the breath measuring device (10), a button (15) that enables the breath measuring device (10) to be switched on and off and to start receiving data, a charge input port (16) that allows the breath measuring device (10) to be charged, and an air outlet opening (17) that allows the exhaled breath to exit the breath measuring device (10). The warnings of the breath measuring device (10) given by the electronic circuit card (14) to the user are information such as the charge status, on-off status of the breath measuring device, etc. After the user presses the button (15), the gas sensors (12) receive the data and transmit it to the mobile device (30).

The portable breath measurement device (10) is a well-being assistant that guides through the mobile device (30) and the server (20) to which it is wirelessly connected, on healthy nutrition, obesity treatment, preparation, and maintenance of an effective sports program.

Gases that can be measured with the gas sensor (12) of the portable breath measuring device (10) are;

Carbon Monoxide (CO): 1-1000 ppm

Nitrogen Dioxide (NO2): 0.05-10 ppm

Ethanol (C2H5OH): 10-500 ppm

Hydrogen (H2): 1-1000 ppm

Ammonia (NH3): 1-500 ppm

Methane (CH4): >1000 ppm

Acetone (C3H6O): >0.10 ppm

The server (20) receives the data received from the breath measuring device (10) via the mobile device (30) and ensures that it is analyzed, and it provides a personalized metabolism and fat burning rate from breath analysis, missing or excess nutrients in the nutrition program, detection of foods that cause digestive problems and their removal from the diet. The server (20) ensures that a personalized nutrition plan is created and its effectiveness is followed in line with the data obtained. The server (20) sends the analysis results back to the mobile device (30), allowing the results, analyzes, and special nutrition plan to be displayed on the mobile device (30). The server (20) performs a number of process steps to analyze the data and create the nutrition plan. The process steps are;

- Wirelessly transmitting the received data to the mobile device (30) after the breath measuring device (10) receives the data, and transmitting the received data to the server (20) by the mobile device (30);
- Analyzing the data received by comparing it with reference values by the server (20), and evaluating the changes in hunger-fullness or repeated daily measurements by the server (20);
- Preparing a nutrition program according to the results of the analysis in line with the data obtained by the server (20);
- Offering menu samples as a recommendation to the user in terms of feeding according to the analysis result in line with the obtained data by the server (20);
- Offering a suggestion to the user as a result of the analysis performed according to the received data by the server (20);
- Displaying the results, analyzes, and special nutrition plan on the mobile device (30) by sending the analysis results, suggested nutrition program, menu samples, and recommendations back to the mobile device (30) by the server (20).

The mobile device (30) transmits the gas data it receives from the breath measuring device (10) to the server (20), and displays the analysis and the nutrition plan created by the server (20) to the user via its interface. The mobile device (30) is preferably a smart phone, and may be any type of the mobile device (30) such as a laptop computer, a tablet, a smart watch, a smart wristband, wearable glasses, etc.

After the breath measuring device (10) is turned on with the button (15), it performs its own calibration and gives a warning to the user with the electronic circuit card (14) when it is ready to blow. The user blows to the breath measuring device (10) at a constant speed for 5-10 seconds. The breath measuring device (10) containing sensors (12) measures the gas values it can measure from this breath, transfers it to the mobile device (30) and records it. The gases measured in the breath are transferred to the mobile device (30) wirelessly, preferably via bluetooth. The mobile device transmits the data to the server (20). The server (20) prepares a nutrition program according to the results of the analysis. Said prepared program is transmitted to the mobile device (30). If the user desires, he/she can monitor his/her compliance with said program and activity with daily measurements from the mobile device (30) interface. The mobile device (30) also has a comprehensive interface in which the user can record the foods consumed daily. Changes in hunger-fullness or daily repeated measurements are evaluated by the server (20) and menu samples are presented to the user as a recommendation in terms of nutrition. The server (20) offers many suggestions to the user as a result of the analysis performed according to the received data. All suggestions made by the server (20) are transmitted to the user via the mobile device (30) interface.

For example, the acetone level in the breath shows the fat burning status, whether the acetone level is at the desired level, and the suitability of diet or exercise can be followed. Also, if, for example, the hydrogen gas in the breath is high; the server (20) offers a suggestion such that "you may have an intolerance (digestive insufficiency) to a food you consume today, it would be beneficial to talk to your doctor/dietician". The suggestion presented by the server (20) is displayed on the mobile device (30).

For example, ketone levels are expected to increase during weight loss, if ketone gas does not rise in the measurement of the person at home, the server (20) determines that there is no fat burning, that he/she needs to reduce the carbohydrates he/she takes, and this suggestion is transmitted to the user via the mobile device (30).

In order to measure acetone gas, which is a ketone substance, a sensor (12) working with semiconductor technology is used to measure acetone gas from the breath. The formation of acetone gas is associated with fat burning metabolism. Acetoacetate, beta hydroxy butyrate, and acetone are produced in the liver to use the fat stored in the fat cells to meet the energy needs of the body. Acetone is excreted from the lungs due to the low molecular weight thereof. Acetone gas measured in the breath is an indicator of ketone production in the liver. Ketone production is an indicator of how much of our body's energy needs are met with fat, and it allows for monitoring this data by measuring it. This measured data is transferred to the mobile device (30). The user can instantly see and monitor whether their metabolism meets the energy source from fat with this mobile device (30). Based on these data, the server (20) provides recommendations to the user regarding daily carbohydrate consumption. If the ketone level is lower than 20, the server (20) offers nutritional recommendations and appropriate menu examples in order to reduce carbohydrate consumption. If the ketone level is above 50, the server (20) offers a nutritional program and appropriate menu examples to protect it. Thus, it helps to control weight with the continuation of fat burning.

For example, if increased NH3 is detected in the breath of someone with a high protein intake, the server (20) suggests the user to reduce their protein consumption. This suggestion offered by the server (20) is displayed with the mobile device (30) interface.

During the use of proteins in the body, nitrogenous compounds are formed as breakdown products from proteins metabolized in the liver. These degradation products, which increase with excess protein intake, cause an increase in NH3 value in the blood and breath and an increase in excretion as urea in the urine. Consistently high protein nutrition, especially for slimming or increasing muscle building, impairs liver and kidney health. The server (20), which detects increased NH3 in the breath, offers menu recommendations with low protein to the user via the mobile device (30).

For example, If increased H or methane gas is detected after a meal, there may be an intolerance to a food, therefore, the server (20) suggests the user via the mobile device (30) that it is recommended that you review the foods you consume during the meal and talk to a specialist.

Foods are fermented by bacteria in the intestine during their digestion, and as a result, short-chain fatty acids are formed. These fatty acids are reused by beneficial bacteria. However, in this process, H and methane gas are formed as side products. This is naturally occurring intestinal gas and some of it is removed from the body by breathing. Some people, due to different reasons (enzyme deficiency, IBS disease, etc.), cannot sufficiently digest dietary carbohydrates such as lactose and produce H and methane gas rather than short-chain fats. These gases impair nutrition and quality of life and make it difficult to lose weight. When increased H and methane are detected in the breath compared to the level of hunger, the server (20) informs the user via the mobile device (30) that there is a digestive problem against the foods he/she consumes during the last meal.

The portable breath measurement device (10) of the system that is the subject of the invention has a non-invasive, sensitive system and a method that can get instant results instead of invasive methods that are laborious and painful for the patient. Since the amount of VOCs in the breath can be affected by metabolic disorders or diseases, the system according to the present invention is considered a safer method in terms of disease diagnosis and monitoring of metabolic status.

The system according to the present invention will also contribute to the reduction of device health expenditures, which will be used to evaluate the metabolic data of the person, especially in the treatment of obesity, and to monitor the effectiveness of the diets applied. The device to be used specifically for the person will provide individual nutrition control with instant and repetitive measurements, as well as the right direction can be made by following the data instantly by the expert. It will contribute to social health and healthy aging by regulating healthy nutrition and metabolic health, preventing chronic diseases, especially diabetes, or supporting treatment processes.

The invention claimed is:

1. A portable breath analysis system that helps healthy eating and weight loss by analyzing respiratory gases taken from a person's breath, characterized in that, comprises;

A breath measuring device having a blowing mouthpiece that allows a user to blow his/her breath, that measures Carbon Monoxide (CO), Nitrogen Dioxide (NO2), Ethanol (C2H5OH), Hydrogen (H2), Ammonia (NH3), Methane (CH4), Acetone (C3H6O) gases simultaneously and instantaneously, a gas sensor for measuring the gases in the breath, a breath chamber, in which the blown breath is transmitted to the gas sensor, an electronic circuit card that configured to wireless transmission of received data to a mobile device and gives the user warnings of the breath measuring device, a button that configured to the breath measuring device to be switched on and off and to start receiving data, a charge input port that allows the breath measuring device to be charged, and an air outlet opening that allows an exhaled breath to exit the breath measuring device, A server that analyzes the data received by the breath measuring device via the mobile device, and configured to personal metabolism and fat burning rate from breath analysis, missing or excess nutrients in a nutrition program, a determination of foods that cause digestive problems and their removal from a diet, that configured to creation of a personalized nutrition plan and monitoring its effectiveness in line with data obtained, that sends analysis results back to the mobile device and displays the results, analyzes, and special nutrition plan on the mobile device, The mobile device that transmits gas data received from the breath measuring device to the server, that takes the analysis results and the nutrition plan created by the server and displays it to the user through its interface.

2. The portable breath analysis system of the breath analysis system according to claim 1, characterized in that, the breath measuring device comprises the gas sensor measuring Carbon Monoxide (CO) gas in a range of 1-1000 ppm.

3. The portable breath analysis system of the breath analysis system according to claim 1, characterized in that, the breath measuring device comprises the gas sensor measuring Nitrogen Dioxide (NO2) gas in a range of 0.05-10 ppm.

4. The portable breath analysis system of the breath analysis system according to claim 1, characterized in that, the breath measuring device comprises the gas sensor measuring Ethanol (C2H5OH) gas in a range of 10-500 ppm.

5. The portable breath analysis system of the breath analysis system according to claim 1, characterized in that, the breath measuring device comprises the gas sensor measuring Hydrogen (H2) gas in a range of 1-1000 ppm.

6. The portable breath analysis system of the breath analysis system according to claim 1, characterized in that, the breath measuring device comprises the gas sensor measuring Ammonia (NH3) gas in a range of 1-500 ppm.

7. The portable breath analysis system of the breath analysis system according to claim 1, characterized in that, the breath measuring device comprises the gas sensor measuring Methane (CH4) gas in a range of >1000 ppm.

8. The portable breath analysis system of the breath analysis system according to claim 1, characterized in that, the breath measuring device comprises the gas sensor measuring Acetone (C3H6O) gas in a range of >0.10 ppm.

9. The portable breath analysis system of the breath analysis system according to claim 1, characterized in that, it comprises the mobile device that allows monitoring a carbohydrate (sugar), fat, and protein consumption of the person by receiving this data from the server by means of transmitting the data obtained from the gases measured by the breath measuring device to the server.

10. The portable breath analysis system of the breath analysis system according to claim 1, characterized in that, the user warnings of the breathe measuring device given to the user by the electronic circuit card are a charge status and on-off status information of the breath measuring device.

11. The portable breath analysis system of the breath analysis system according to claim 1, characterized in that, the mobile device configured to be a smart phone, a laptop, a tablet, a smart watch, a smart wristband, wearable glasses.

12. The portable breath analysis system of the breath analysis system according to claim 1, characterized in that, the mobile device is preferably a smartphone.

13. An analysis method of the breath analysis system according to claim 1, in order to analyze the data and create the nutrition plan, the server comprises the process steps of, Wirelessly transmitting the received data to the mobile device after the breath measuring device receives the data, and transmitting the received data to the server by the mobile device;

Analyzing the data received by comparing it with reference values by the server, and evaluating changes in hunger-fullness or repeated daily measurements by the server;

Preparing a nutrition program according to the results of the analysis in line with the received data by the server;

Offering menu samples as a recommendation to the user in terms of feeding according to the analysis result in line with the received data by the server;

Offering a suggestion to the user as the result of the analysis performed according to the received data by the server;

Sending the analysis results, suggested nutrition program, menu samples and suggestions back to the mobile device by the server, Displaying results, analysis, and custom nutrition plan from the mobile device interface.

14. The analysis method of the breath analysis system according to claim 13, characterized in that, in the process step of offering a suggestion to the user as the result of the analysis performed according to the received data by the server, it comprises the process step of, offering a suggestion such that "you may have an intolerance (digestive insufficiency) to a food you consume today, it would be beneficial to talk to your doctor/dietician" by the server if the hydrogen gas in the breath is high, displaying the suggestion offered by the server with the mobile device interface.

15. The analysis method of the breath analysis system according to claim 13, characterized in that, in the process step of offering a suggestion to the user as the result of the analysis performed according to the received data by the server, it comprises the process step of;

offering a suggestion to the user that he/she does not burn fat and that he/she should reduce carbohydrates by the server if ketone gas does not increase in the measurement as the result of the analysis, transmitting this suggestion to the user via the interface by the mobile device.

16. The analysis method of the breath analysis system according to claim 13, characterized in that, in the process step of offering menu samples as a recommendation to the user in terms of feeding according to the analysis result in line with the received data by the server, it comprises the process step of;

Offering menu samples by the server in accordance with nutritional recommendations to reduce carbohydrate consumption, if a ketone level is lower than 20, Offering a nutritional program and appropriate menu examples to protect the ketone level is above 50 by the server if the ketone level is above 50, Displaying the suggestion offered by the server with the mobile device interface.

17. The analysis method of the breath analysis system according to claim 13, characterized in that, in the process step of analyzing the data received by comparing it with reference values by the server, and evaluating the changes in hunger-fullness or repeated daily measurements by the server, it comprises the process step of, Suggesting the user to reduce their protein consumption by the server if increased NH3 is detected in the breath of someone with a high protein intake, Displaying the suggestion offered by the server with the mobile device interface.

18. The analysis method of the breath analysis system according to claim 13, in the process step of offering menu samples as a recommendation to the user in terms of feeding according to the analysis result in line with the received data by the server, the server provides menu recommendations with low protein to the user via the mobile device if increased NH3 is detected in the breath.

19. The analysis method of the breath analysis system according to claim 13, characterized in that, in the process step of offering a suggestion to the user as the result of the analysis performed according to the received data by the server; the server informs the user via the mobile device that he/she has a digestive problem against the foods he/she consumes during the last meal when increased H and methane are detected in the breath compared to a hunger level.

20. The analysis method of the breath analysis system according to claim 13, characterized in that, in the process step of offering a suggestion to the user as the result of the analysis performed according to the received data by the server; the server advises the user via the mobile device that it is recommended that you review the foods you consume during a meal and talk to an expert if increased H or methane gas is detected after the meal.

* * * * *